(12) United States Patent
Eh et al.

(10) Patent No.: US 6,573,391 B1
(45) Date of Patent: Jun. 3, 2003

(54) 1,4-DIOXACYLCLOALKANE-2-ONE AND 1,4-DIOXACYCLOALKENE-2-ONE

(75) Inventors: Marcus Eh, Holzminden (DE); Peter Wörner, Holzminden (DE)

(73) Assignee: Haarmann & Reimer GmbH (DE)

( * ) Notice: Subject to any disclaimer, the term of this patent is extended or adjusted under 35 U.S.C. 154(b) by 0 days.

(21) Appl. No.: 10/088,812

(22) PCT Filed: Sep. 14, 2000

(86) PCT No.: PCT/EP00/08973

§ 371 (c)(1),
(2), (4) Date: Mar. 21, 2002

(87) PCT Pub. No.: WO01/23373

PCT Pub. Date: Apr. 5, 2001

(30) Foreign Application Priority Data

Sep. 27, 1999 (DE) .......................................... 199 46 128

(51) Int. Cl.$^7$ .......................... C07D 323/00; A61K 7/46
(52) U.S. Cl. .......................... 549/267; 512/12; 560/183
(58) Field of Search .......................... 549/267; 512/12; 560/183

(56) References Cited

U.S. PATENT DOCUMENTS 4,490,404 A   12/1984   Van Loveren et al. ...... 426/536

FOREIGN PATENT DOCUMENTS

EP          884 315          12/1998
JP          10/175882        6/1998

OTHER PUBLICATIONS

Fajfer, Andrzej et al, 'Method for manufacturing a new derivs. of 3–oxahexadecanolide' CA 116:59418 (1992).*
Paquot, Charles et al. 'Synthesis and properties of the isomeric 14–hydroxy–4–oxatetradecanoic and 2–methyl–13–hydroxy–3–oxatridecanoic acids' CA 67:53587 (1967).*
Common Fragrance and Flavor Materials, 3$^{rd}$ edition, (month unavailable) 1997, pp. 67–68 & 117–122, K. Bauer, D. Garbe, H. Surburg, "Single Fragrance and Flavor Compounds".
Ernährungs Umschau 43, (month unavailable) 1996, pp. 442–449, Gerhard Rimkus und Hubertus Brunn, "Synthetische Moschusduftstoffe–Anwendung, Anreicherung in der Umwelt und Toxikologie".
Ernährungs–Umschau 44 (month unavailable) 1997, pp. 4–9, Hubertus Brunn und Gerhard Rimkus, "Synthetische Moschusduftstoffe–Anwendung, Anreicherung in der Umwelt und Toxikologie".
Tetrahedron Letters, No. 39, (month unavailable) 1976, pp. 3535–3536, S. Czernecki, C. Georgoulis et C. Provelenghiou, "Nouvelle Methode De Benzylation D'Hydroxyles Glucidiques Encombres".
J. Org. Chem. 63, (month unavailable) 1998, pp. 3160–3161, Steven D. Burke, Raymond A. Ng, James A. Morrison and Michael J. Alberti, "Tandem Glycolate Claisen Rearrangement/Ring–Closing Metathesis: A Stereochemically General Synthesis of Substituted Dihydropyran–2–carboxylates".
Tetrahedron Letters, vol. 21, (month unavaliable) 1980, pp. 1715–1718, Didier Villemin, "Synthese De Macrolides Par Metathese".
Synthesis, Jul. 1997, pp. 792–793, Alois Fürstner and Klaus Langemann "Macrocycles by Ring–Closing Metathesis".
Synlett, Aug. 1997, pp. 1010–1012, Alois Fürstner and Thomas Müller, "The First Synthesis of a 10–Membered Ring by Olefin Metathesis: Jasmine Ketolactone".
Tetrahedron Letters, vol. 29, No. 33, (month unavailable) 1988, pp. 4139–4142, Noriyuki Nakajima, Kiyoshi Horita, Reiko Abe, and Osamu Yonemitsu, "MPM (4–Methoxybenzyl) Protection of Hydroxy Functions Under Mild Acidic Conditions".
Tetrahedron Letters, 39, (month avaiable) 1998, pp. 4223–4226, Pavel Krasik, "Synthesis of Sterically Hindered Esters via Titanium Catalyzed Transesterification".
**Chemical Abstracts, vol. 116, No. 28, 1992 Columbus, Ohio, US; abstract no. 59418j, p. 869; XP002163324 abstract & PL 153 102 A (Politechnika Lodzka) Mar. 29, 1991.
**Chemical Abstracts, vol. 67, No. 23, 1967 Columbus, Ohio, US; abstract no. 53587m, CH Paquot et al.: "Synthesis A. Properties of the Isomeric 14–Hydroxy–4–Oxatetradecanoic A. 2–Methyl–13–Hydroxy–3–Oxatridecanoci Acids." p. 5019; XP002163325 abstract & REV. FR. CORPS GRAS, vol. 14, No. 3, 1967, pp. 167–73, France.

* cited by examiner

Primary Examiner—Amelia Owens
(74) Attorney, Agent, or Firm—Pendorf & Cutliff

(57) ABSTRACT

The present invention relates to novel macrocyclic compounds, and to their preparation and use in perfumes. Specifically, the present invention relates to novel 1,4-dioxacycloalkan-2ones and 1,4-dioxzcycloaken-2-ones.

18 Claims, No Drawings

1,4-DIOXACYLCLOALKANE-2-ONE AND 1,4-DIOXACYCLOALKENE-2-ONE

FIELD OF THE INVENTION

The invention relates to novel 1,4-dioxacycloalkan-2-ones and 1,4-dioxacycloalken-2-ones, and to their preparation and use in functional perfumery and in fine perfumery.

BACKGROUND OF THE INVENTION

Compounds with a musk odor are sought-after components in the fragrance industry. They are characterized both by their property of imparting radiance to perfume compositions and also by their ability to act as fixative. For this reason, musk fragrances are nowadays used in many perfume compositions.

Typical musk fragrances are characterized by a macrocyclic ring having 13 to 17 carbon atoms which carries a ketone or an ester as functional group. Moreover, macrocyclic musk fragrances which carry two functional group are also known, e.g. 1,7-dioxacycloalkan-8-ones (EP A 884, 315). However, the functional groups of these molecules are distributed over both hemispheres of macrocycles. Preference is, however, given to macrocyclic compounds in which the functional groups are concentrated in one part of the molecule since, in so doing, a stronger bond to the active center of the receptor and, consequently, a lower threshold value can be expected.

Because the costs of starting materials for the preparation are sometimes high and because of the extremely high synthesis complexity, the number of macrocyclic compounds available to the perfumer for the composition of perfumes is relatively limited (K. Bauer, D. Garbe, H. Surburg, Common Fragrance and Flavor Materials, Wiley-VCH, 3$^{rd}$ Edition, 1997, 67 to 68 and 117 to 122). There is an urgent need for further macrocyclic compounds which can be prepared in an efficient synthesis from favorable starting materials and, moreover, extend the perfumer's options with their original scent properties.

The class of nature-similar macrocyclic musk fragrances will become more and more important in the future since the synthetic musk compounds of the nitroaromatic and polycyclic series are persistent and lipophilic, meaning that these compounds accumulate in aquatic food chains and fatty tissue (H. Brunn, G. Rimkus, Ernährungs-Umschau 1996, 43, 442 to 449; H. Brunn, G. Rimkus, Ernährungs-Umschau 1997, 44, 4 to 9).

SUMMARY OF THE INVENTION

It was therefore the object to extend the raw material palette available for composing perfume through novel macrocyclic musk compounds with original odiferous properties.

Furthermore, it should be possible to prepare the novel musk fragrances in a cost-effective manner.

DETAILED DESCRIPTION OF THE INVENTION

We have now found novel 1,4-dioxacycloalkan-2-ones and 1,4-dioxacycloalken-2-ones of the formula

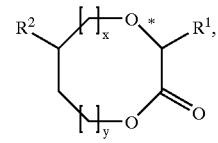

(I)

in which
the dashed bond is a single or E/Z double bond,
where in the case of a double bond being present in the ring, the compounds can be in the E and Z form, and
compounds with a chiral center can be either in the (R) or (S) form, or else can be present as an enantiomer mixture,
$R^1$ and $R^2$ are identical or different and are hydrogen or lower alkyl,
x is a saturated alkylene chain having 1 to 4 carbon atoms and
y is a saturated alkylene chain having 4 to 10 carbon atoms,
where saturated compounds
in which $R^1$ and $R^2$ are hydrogen and x+y=11 carbon atoms and
in which $R^1$ is methyl and $R^2$ is hydrogen and x+y=8 carbon atoms, are excluded.

Lower alkyl generally means a saturated hydrocarbon radical having 1 to 6 carbon atoms. Examples which may be mentioned are: methyl, ethyl, propyl, isopropyl, butyl, isobutyl, pentyl, isopentyl, hexyl and isohexyl.

Preferred radicals are hydrogen, methyl and ethyl.

An alkylene chain having 1 to 4 carbon atoms generally means methylene, ethylene, propylene and butylene.

Preference is given here to: methylene, ethylene and butylene.

An alkylene chain having 4 to 10 carbon atoms generally means butylene, pentylene, hexylene, heptylene, octylene, nonylene and decylene.

Preference is given here to: butylene, octylene and nonylene.

The novel 1,4-dioxacycloalkan-2-ones and 1,4-dioxacycloalken-2-ones according to the invention accordingly include 14- to 18-membered saturated or unsaturated, unsubstituted or lower-alkyl-substituted 1,4-dioxacycloalkan-2-ones and 1,4-dioxacycloalken-2-ones.

Specifically, mention may be made of the following 1,4-dioxacycloalkan-2-ones and 1,4-dioxacycloalken-2-ones:
1,4-dioxa-(E/Z)-9-cyclotetradecen-2-one
1,4-dioxacyclotetradecan-2-one
3-methyl-1,4-dioxa-(E/Z)-6-cyclopentadecen-2-one
3-methyl-1,4-dioxacyclopentadecan-2-one
1,4-dioxa-(E/Z)-6-cyclopentadecen-2-one
1,4-dioxacyclopentadecan-2-one
3-methyl-1,4-dioxa-(E/Z)-6-cyclohexadecen-2-one
3-methyl-1,4-dioxacyclohexadecan-2-one
1,4-dioxa-(E/Z)-6-cyclohexadecen-2-one
1,4-dioxacyclohexadecan-2-one
1,4-dioxa-(E/Z)-7-cyclohexadecen-2-one
1,4-dioxa (E/Z)-7-cycloheptadecen-2-one
3-methyl-1,4-dioxa-(E/Z)-7-cyclohexadecen-2-one
3-methyl-1,4-dioxa-(E/Z)-7-cycloheptadecen-2-one
3-methyl-1,4-dioxacycloheptadecan-2-one The 1,4-dioxacycloalkan-2-ones and 1,4-dioxacycloalken-2-ones according to the invention in which the functional groups are in close proximity to one another achieve said object in an ideal manner. As well as perfumistically interesting musk-like odor notes, they are characterized by very good adhesion, coupled with a low threshold value.

The saturated 1,4-dioxacycloalkan-2-ones, methyl-substituted in the 3 position, in particular 3-methyl-1,4-dioxacyclopentadecan-2-one and 3-methyl-1,4-dioxacyclohexadecan-2-one, have particularly attractive olfactory odor properties. They are characterized by a sweet, woody-ambergris, animalic, erogenous and thus very natural musk note. The olfactory profile of the unsaturated 3-methyl-1,4-dioxacyloalken-2-ones is very similar to that of the saturated compounds, although the intensity is lower. For comparison, the analogous 1,4-dioxacycloalkan-2-ones and 1,4-dioxacycloalken-2-ones without methyl substitution in the 3 position have been synthesized. Surprisingly, in the case of the unsaturated 1,4-dioxacycloalken-2-ones, the erogenous and animalic aspects are pushed into the background in favor of metallic, pressing iron-like odor descriptions. The saturated 1,4-dioxacycloalkan-2-ones, by contrast, and here in particular 1,4-dioxacyclohexadecan-2-one are characterized again by a very nice natural musk-like character.

In contrast to the known 1,4-dioxacycloheptadecan-2-one and 3-methyl-1,4-dioxacyclotetradecan-2-one, the 1,4-dioxacycloalkan-2-ones and 1,4-dioxacycloalken-2-ones according to the invention surprisingly have a very much more natural musk note, coupled with nitromusk and ambrette musk aspects.

We have found a process for the preparation of novel 1,4-dioxacycloalkan-2-ones and 1,4-dioxacycloalken-2-ones of the formula

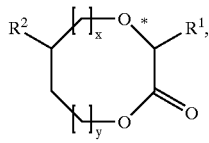

(I)

in which the dashed bond is a single or E/Z double bond, where in the case of a double bond being present in the ring, the compounds can be in the E and Z form, and compounds with a chiral center can be either in the (R) or (S) form, or else can be present as an enantiomer mixture, $R^1$ and $R^2$ are identical or different and are hydrogen or lower alkyl, x is a saturated alkylene chain having 1 to 4 carbon atoms and y is a saturated alkylene chain having 4 to 10 carbon atoms, where saturated compounds in which $R^1$ and $R^2$ are hydrogen and x+y=11 carbon atoms and in which $R^1$ is methyl and $R^2$ is hydrogen and x+y=8 carbon atoms, are excluded, found, which is characterized in that alkylcarboxylic acids or esters thereof which can be derivatized in the 2 position and are of the formula

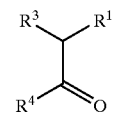

in which $R^1$ has the meaning given above, and $R^3$ is OH, Cl, Br and $R^4$ is OH, OMe or OEt, are used, which, in the 1st step, are etherified, in a 2nd step are esterified and in a 3rd step the ring is closed by olefine metathesis to give the unsaturated 1,4-dioxacycloalken-2-ones, which are then optionally hydrogenated in a 4th step to give the saturated 1,4-dioxacycloalkan-2-ones.

In the 1st step, where $R^3$=OH and $R^4$=OMe or OEt, deprotonation is carried out with one equivalent of sodium hydride as base in tetrahydrofuran as solvent. 1.5 equivalents of the [lacuna],ω-alkene halide are then added, after which the reaction mixture is refluxed, giving the 2-alkenyloxycarboxylic esters (Tetrahedron Lett. 1976, 17, 3535).

In the case of the α-halocarboxylic acids ($R^3$=Cl, Br and $R^4$=OH) as starting compounds, 2 to 3 equivalents of sodium hydride are required, the α,ω-alkenol firstly being deprotonated before the α-halocarboxylic acid is added. This mixture too is refluxed in order to obtain the 2-alkenyloxycarboxylic acids (J. Org. Chem. 1998, 63, 3160).

The 2-alkenyloxycarboxylic acids ($R^4$=OH) synthesized in the manner described above are esterified in the 2nd step with the addition of from 1 to 3 equivalents of the corresponding α,ω-alkenol and 0.1 to 5 mol % of p-toluenesulfonic acid with a water separator using toluene as entrainer to give the doubly terminally unsaturated 2-alkenyloxycarboxylic alkenyl esters.

If the 2-alkenyloxycarboxylic esters ($R^4$=OMe, OEt) are present, these are firstly hydrolyzed with 1.5 to 2 equivalents of LiOH in methanol/water (ratio:3:1) in order then to be esterified with 1 to 3 equivalents of the corresponding α,ω-alkenol and 0.1 to 5 mol % of 0p-toluenesulfonic acid with a water separator to give the doubly terminally unsaturated 2-alkenyloxycarboxylic alkenyl esters.

The intermediates which form here are the novel doubly terminally unsaturated 2-alkenyloxycarboxylic alkenyl esters of the formula

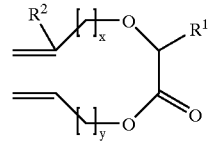

in which $R^1$, $R^2$, x and y have the meaning given above.

The 1,4-dioxacycloalken-2-ones according to the invention are prepared (3rd step) starting from the doubly terminally unsaturated 2-alkenyloxycarboxylic alkenyl esters in a ring closure olefin metathesis (U.S. Pat. No. 4,490,404; D. Tetrahedron lett., 1980, 21, 1715; JP 10 175,882). For this, the 2-alkenyloxycarboxylic alkenyl ester is refluxed for one hour in a 0.01 to 0.003 molar dichloromethane solution with 0.1 to 0.5 equivalents of titanium tetraisopropoxide. The subsequent addition of from 0.5 to 5 mol % of benzylidene-bis-tricyclohexylphosphine)-dichlororuthenium (Grubbs catalyst) and reheating at reflux temperature for 8 to 48 hours (Synthesis, 1997, 792; Synlett, 1997, 1010) produces the 1,4-dioxacycloalken-2-ones according to the invention.

The hydrogenation (4th step) at standard hydrogen pressure and room temperature with 1 to 5% by weight of Pd/C in isopropanol produces the 1,4-dioxacycloalkan-2-ones according to the invention starting from the 1,4-dioxacycloalken-2-ones according to the invention.

The process according to the invention can be illustrated using the example of 3-methyl-1,4-dioxacyclopentadecan-2-one by the following equation:

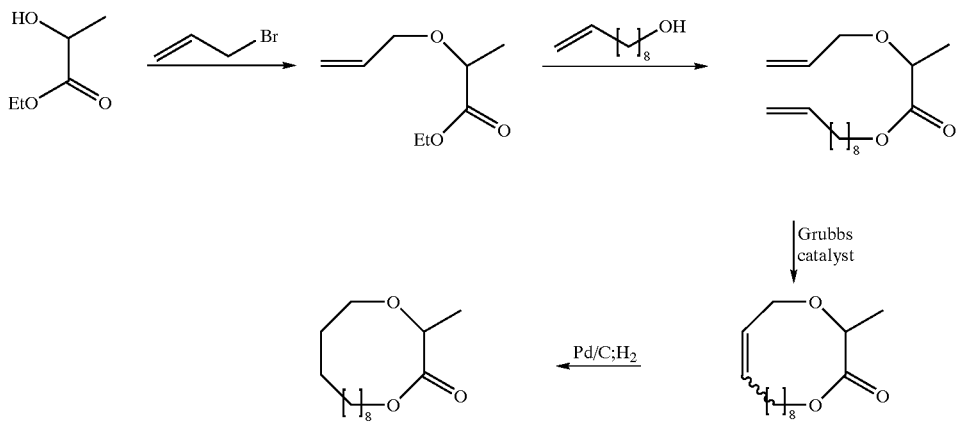

We have found a further process for the preparation of the novel chiral 3-alkyl-1,4-dioxacycloalkan-2-ones and 3-alkyl-1,4-dioxacycloalken-2-ones of the formula

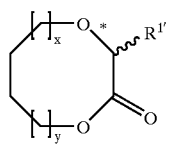

(II)

in which the dashed bond is a single or E/Z double bond, where in the case of a double bond being present in the ring, the compounds can be in the E and Z form, and the compounds with a chiral center are present in the (R) or (S) form, $R^1$ is lower alkyl and x is a saturated alkylene chain having 1 to 4 carbon atoms and y is a saturated alkylene chain having 4 to 10 carbon atoms, which is characterized in that the starting materials used are (S)-2- or (R)-2-hydroxycarboxylic alkyl esters of the formula

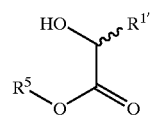

in which $R^1$ has the meaning given above, and $R^5$ is a $C_1$ to $C_8$ alkyl radical, which are etherified in a 1st step under acidic, nonracemizing conditions, are transesterified in a 2nd step under Lewis acid catalysis and in a 3rd step the ring is closed by olefin metathesis to give the unsaturated 3-alkyl-1,4-dioxacycloalken-2-ones, which are then optionally hydrogenated in a 4th step to give the saturated 3-alkyl1,4-dioxacycloalkan-2-ones.

In the 1st step, the O-alkylation of the (R)- or (S)-2-hydroxycarboxylic alkyl esters is carried out via the trichloroacetimidate methods (Tetrahedron Lett., 1988, 29, 4139–4142). For this, 2 to 3 equivalents of the alkenyl trichloroacetimidate and 5 to 15 mol % of trifluoromethane-sulfonic acid are added to the chiral 2-hydroxycarboxylic alkyl esters in cyclohexane. After 16 to 24 hours at room temperature, the chiral (R)- or (S)-2-alkenyloxycarboxylic alkyl esters are obtained. The enantiomeric excesses of these compounds are ≧95%.

In the subsequent transesterification (2nd step), the chiral 2-alkenyloxycarboxylic ester is reacted with 1 to 3 equivalents of the corresponding [lacuna],ω-alkenol, with the addition of from 1 to 10 mol % of titanium tetraisopropoxide (Tetrahedron Lett., 1998, 4223–4226). This gives the chiral, doubly terminally unsaturated 2-alkenyloxycarboxylic alkenyl esters.

The chiral doubly terminally unsaturated 2-alkenyloxycarboxylic alkenyl esters of the formula

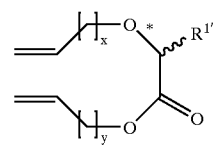

in which $R^{1'}$, x and y have the meaning given above are novel.

The enantiomeric excesses of these compounds are ≧95%.

The preparation of the novel chiral 3-alkyl-1,4-dioxacycloalken-2-ones and 3-alkyl-1,4-dioxacycloalkan-2-ones is carried out in accordance with the methods described above, via ring closure olefin metathesis (3rd step) and subsequent hydrogenation (4th step).

The enantiomeric excesses of the saturated 3-alkyl-1,4-dioxacycloalkan-2-ones are ≧95%.

The process according to the invention can be illustrated using the example of (S)-(−)-3-methyl-1,4-dioxacyclopentadecan-2-one by the following equation:

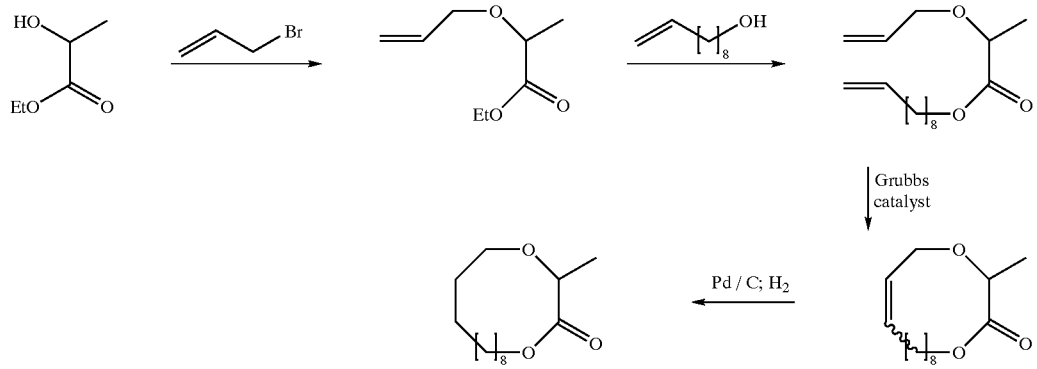

Specifically, the following chiral 3-alkyl-1,4-dioxacycloalkan-2-ones and 3-alkyl-1,4-dioxacycloalken-2-ones may be mentioned:
(S)-(−)-3-methyl-1,4-dioxa-(E/Z)-6-cyclopentadecen-2-one
(S)-(−)-3-methyl-1,4-dioxacyclopentadecan-2-one
(S)-(−)-3-methyl-1,4-dioxa-(E/Z)-6-cyclohexadecen-2-one
(S)-(−)-3-methyl-1,4-dioxacyclohexadecan- 2-one
(R)-(+)-3-methyl-1,4-dioxa-(E/Z)-6-cyclopentadecen-2-one
(R)-(+)-3-methyl-1,4-dioxacyclopentadecan-2-one
(R)-(+)-3-methyl-1,4-dioxa-(E/Z)-6-cyclohexadecen-2-one
(R)-(+)-3-methyl-1,4-dioxacyclohexadecan-2-one The novel 1,4-dioxacycloalkan-2-ones and 1,4-dioxacycloalken-2-ones can be used here as individual substances in a large number of products; they can be particularly advantageously combined with other fragrances to give new types of perfume compositions.

By using the novel 1,4-dioxacycloalkan-2-ones and 1,4-dioxacycloalken-2-ones, it is generally possible, even in a low concentration, to achieve fine, erogenous musk notes in the resulting perfume compositions, the overall odor impression being remarkably harmonized, the radiance be detectably increased and the fixing, i.e. the adhesive power of the perfume oil, being considerably intensified.

Examples of fragrances with which the novel 1,4-dioxacycloalkan-2-ones and 1,4-dioxacycloalken-2-ones can be advantageously combined are given, for example, in S. Arctander, Perfume and Flavor Materials, Vol. I and II, Montclair, N. J., 1969, Selbstverlag oder K. Bauer, D. Garbe and H. Surburg, Common Fragrance and Flavor Materials, 3$^{rd}$. Ed., Wiley-VCH, Weinheim 1997.

Specifically, mention may be made of:
extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange-flower absolute; orange oil; origanum oil; palmarosa oil; patchouli oil; perilla oil; Peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulfur-containing compounds, such as, for example, 3-methylthiohexanol; 3-methylthiohexyl acetate; 3-mercapto-hexanol; 3-mercaptohexyl acetate; 3-mercaptohexyl butyrate; 3-acetylthiohexyl acetate; 1-menthene-8-thiol; of aliphatic nitriles, such as, for example, 2-nonenenitrile; 2-tridecenenitrile; 2,12-tridecienenitrile; 3,7-dimethyl-2,6-octadienenittile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxy-acetate ; methyl 3,7-dimethyl-2,6-octadienoate;

of acyclic terpene alcohols, such as, for example, citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5- octadien-2-ol; 3,7-dimethyl-4,6-octadien-3-ol; 3,7-dimethyl- 1,5,7-octatrien-3-ol 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H -2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethyl-cyclohexanol; 3-isocamphylcyclohexanol; 2,6,9-trimethyl-Z2,Z5,E9-cyclo dodecatrien-1-ol; 2-isobutyl-4-methyltetrahydro-2H-pyran-4-ol;

of cycloaliphatic alcohols, such as, for example, alpha,3,3-trimethylcyclohexyl -methanol; 2-methyl-4-(2,2,3-trimethyl-3-cyclopent-1-yl)butanol; 2-methyl-4-(2,2,3-trimethyl-3-cyclopent- 1-yl)-2-buten-1-ol; 2-ethyl-4-(2,2,3-trimethyl-3-cyclopent- 1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyl -dodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexene-carbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclo-hexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexa-hydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclo-hexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl) ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxanes; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenyl-acetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amyl-cinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)-propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)-ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnmate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methy N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl) phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-oide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The perfume oils comprising the 1,4-dioxacycloalkan-2-ones and 1,4-dioxacycloalken-2-ones according to the invention can be used in liquid form, neat or diluted with a solvent for perfumings. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate etc.

In addition, the perfume oils comprising the 1,4-dioxacycloalkan-2-ones and 1,4-dioxacycloalken-2-ones according to the invention can be adsorbed on a carrier which serves both to distribute the fragrances finely within the product and to release them in a controlled manner during use. Such carriers can be porous inorganic materials such as light sulfate, silica gels, zeolites, gypsums, clays, clay granules, gas concrete etc. or organic materials such as woods and cellulose-based substances.

The perfume oils comprising the 1,4-dioxacycloalkan-2-ones and 1,4-dioxacycloalken-2-ones according to the invention can also be microencapsulated, spray dried, in the form of inclusion complexes or in the form of extrusion products and be added in this form to the product to be perfumed.

The properties of the perfume oils modified in this way can optionally be further optimized by "coating" with suitable materials with regard to a more targeted scent release, for which purpose preference is given to using wax-like polymers, such as, for example, polyvinyl alcohol.

The microencapsulation of the perfume oils can, for example, be carried out by the "coacervation method" using capsule materials made from, for example, polyurethane-like substances or soft gelatin. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g. water. Extrusion products can arise by melting the perfume oils with a suitable wax-like substance and by extrusion with subsequent solidification, optionally in a suitable solvent, e.g. isopropanol.

In perfume compositions, the amount of 1,4-dioxacycloalkan-2-ones and 1,4-dioxacycloalken-2-ones according to the invention used is 0.05 to 50% by weight, preferably 0.5 to 20% by weight, based on the total perfume oil.

The perfume oils comprising the 1,4-dioxacycloalkan-2-ones and 1,4-dioxacycloalken-2-ones according to the invention can be used in concentrated form, in solutions or in the above-described modified form for the preparation of, for example, perfume extracts, eaux de parfum, eaux de toilette, aftershaves, eaux de cologne, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare compositions, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, such as, for example, hairsprays, hair gels, hairsetting lotions, hair rinses, permanent and semipermanent hair colorants, hair-shaping compositions, such as cold waves and hair-smoothing compositions, hair tonics, hair creams and lotions, deodorants and antiperspirants, such as, for example, underarm sprays, roll-ons, deodorant sticks, deodorant creams, products in decorative cosmetics, such as, for example, eyeshadows, nail varnishes, foundations, lipsticks, mascara, and of candles, lamp oils, joss-sticks, insecticides, repellents, propellants.

One important use of the 1,4-dioxacycloalkan-2-ones and 1,4-dioxacycloalken-2-ones according to the invention is in the perfuming of soaps and laundry detergents because of their stability in the alkaline range. In the case of the use in laundry detergent perfumings, the 1,4-dioxacycloalkan-2-ones and 1,4-dioxacycloalken-2-ones according to the invention are distinguished by a substantivity which is greater than that of fragrances used hitherto, i.e. by increased absorptive power and increased adhesion of the fragrance to the washed fibers.

The compounds below illustrate the invention:

EXAMPLES

Example 1

1,4-Dioxacyclotetradecan-2-one

Hex-5-enyl 2-bromoacetate: 6.2 g (30 mmol) of DCC are added to a solution, cooled to 0° C., of 4.1 g (30 mmol) of bromoacetic acid, 250 mg (3 mmol) of DMAP and 3.3 g (33 mmol) of 5-hexen-1-ol in 30 ml of $CH_2Cl_2$. When the addition is complete, the mixture is left to reach room temperature and stirred overnight. If the reaction is complete, the precipitated urea derivative is filtered off, the filtrate is concentrated by evaporation and the residue is taken up in n-pentane. The mixture is then filtered again and the filtrate is then washed twice with 0.5N HCl and once with saturated $NaHCO_3$ solution. The resulting crude product is used in the next reaction without further purification.

Hex-5-enyl 2-(5-hexenyloxy)-acetate (x, y=4, $R^1$, $R^2$=H): 3,5 g (34 mmol) of 5-hexen-1-ol, dissolved in 25 ml of THF, are added dropwise to a suspension of 0.95 g (28 mmol) of NaH in 20 ml of THF. When the addition is complete, 4.8 g (23 mmol) of hex-5-enyl 2-bromoacetate, dissolved in 15 ml of THF, are added dropwise. The mixture is then refluxed overnight. When the reaction is complete, the mixture is left to cool and quenched with 2N HCl. After the phases have separated, the aqueous phase is extracted again with $Et_2O$ and twice with EtOAc. The combined organic phases are dried over $Na_2SO_4$, filtered and evaporated on a rotary evaporator. The crude product is purified on silica gel (cyclohexane/EtOAc=40:1; $R_f$=0.26), giving, as product, a colorless oil in a yield of 4.8 g (67% over 2 stages).

$^1$H-NMR (200 MHz, $CDCl_3$): δ(ppm)=1.38–1.56 (m, 4H), 1.56–1.76 (m, 4H), 2.0–2.16 (m, 4H), 3.51 (t, J=6.4 Hz, 2H), 4.07 (s, 2H), 4.17 (t, J=6.4 Hz, 2H), 4.99–5.08 (m, 4H), 5.73 (ddd, J=17.2, 10.2, 5.8 Hz, 1H), 5.86 (ddd, J=17.2, 10.2, 5.8 Hz, 1H).

$^{13}$C-NMR (50 MHz, $CDCl_3$): δ(ppm)=25.0, 25.2, 27.9, 28.9, 33.2, 33.4, 64.6, 68.2, 71.6, 114.5, 114.8, 138.1, 138.4, 170.5

The ring closure olefin metathesis and subsequent hydrogenation were carried out analogously to the procedures described under Example 2.1. Only the spectroscopic data are thus given here:

1,4-dioxa-(E/Z)-9-cyclotetradecen-2-one (x, y=4, $R^1$, $R^2$=H)

Odor: woody, cedary, patchouli, musk.

Isomerism details: excess:deficit isomer $^1$H-NMR (200 MHz, $CDCl_3$): δ(ppm)=1.33–1.83 (m, 8H), 1.95–2.16 (m, 4H), 3.53 (t, J=6.5 Hz, 2H), 4.07:4.05 (s, 2H), 4.17–4.33 (m, 2H), 5.25–5.70 (m, 2H).

$^{13}$C-NMR (50 MHz, $CDCl_3$): δ(ppm)=25.2, 25.4, 25.6, 26.4, 26.7, 27.9, 63.8:64.6, 69.6: 68.9, 70.7, 71.7, 129.6:130.7, 130.0:131.3, 171.2.

1,4-dioxacyclotetradecan-2-one (x, y=4, $R^1$, $R^2$=H)

Odor: woody, patchouli, musk, erogenous, metallic, reminiscent of a hot iron.

$^1$H-NMR (200 MHz, $CDCl_3$): δ(ppm)=1.27–1.56 (m, 12H), 1.60–1.77 (m, 2H), 3.53 (t, J=6.4 Hz, 2H), 4.09 (s, 2H), 4.26 (dd, J=5.42, 4.42 Hz, 2H).

$^{13}$C-NMR (50 MHz, $CDCl_3$): δ(ppm)=23.9, 24.0, 24.6, 25.3, 25.5, 25.6, 26.9, 27.5, 64.8, 69.4, 70.4, 170.9.

Example 2.1

(RS)-3-Methyl-1,4-dioxacyclopentadecan-2-one

Ethyl (RS)-2-allyloxy-propionate (x=1, Y=OEt, $R^1$=Me, $R^2$=H): 23.6 g (0.2 mol) of ethyl (S)-(−)-lactate, dissolved in 100 ml of THF, are added to a suspension of 8.0 g (0.2 mol) of NaH in 150 ml THF. When the addition is complete, 36.3 g (0.3 mol) of allyl bromide, dissolved in 10 ml of THF, are added dropwise. Some KI is then added and the mixture is refluxed for 16 h. The mixture is then cooled and the reaction is quenched with 100 ml of 2N HCl. The aqueous phase is extracted twice more with $Et_2O$ before the combined organic phases are dried over $Na_2SO_4$. The mixture is then filtered and the filtrate is evaporated to dryness on a rotary evaporator, giving 31.7 g of crude product (GC purity 89.0%), which is used in the next reactions without further purification.

Dec-9-enyl (RS)-2-allyloxy-propionate (x=1, y=8, $R^1$=Me, $R^2$=H): 3,5 g of crude ethyl (RS)-2-allyloxy-propionate are introduced into 24 ml of $MeOH/H_2O$=3:1, cooled to 0° C., and then 2.2 g (30 mmol) of LiOH·$H_2O$ are added in portions. The mixture is further stirred for 5 minutes before the ice cooling is removed and the mixture is stirred for a further 1 h at room temperature. Methanol is then removed on a rotary evaporator and the residue is taken up in water. The aqueous phase is firstly extracted with $Et_2O$ in order then to be acidified to pH 1 with 6N HCl. The aqueous phase is then saturated with NaCl and extracted three times with EtOAc. The combined organic phases are dried over $Na_2SO_4$, filtered and freed from solvent on a rotary evaporator. The resulting carboxylic acid is dissolved in 40 ml of toluene and treated with 4.7 g (30 mmol) of 9-decen-1-ol and 0.38 g (2 mmol) of p-toluenesulfonic acid. The mixture is then heated using a water separator until visible amounts of water no longer separate out. After cooling to room temperature, the reaction solution is once again wash ed with saturated $NaHCO_3$ solution, then dried over $Na_2SO_4$, filtered and freed from solvent on a rotary evaporator. Flash chromatography (cyclohexane/EtOAc= 20:1, $R_f$=0.31) over silica gel gives 2.8 g (52.2%) of dec-9-enyl (RS)-2-allyloxy-propionate as a colorless oil.

$^1$H-NMR (200 MHz, $CDCl_3$): δ(ppm)=1.25–1.40 (m, 10H), 1.42 (d, J=6.9 Hz, 3H), 1.57–1.74 (m, 2H), 1.97–2.13 (m, 2H), 3.94 (ddd, J=12.5, 5.9, 1.7 Hz, 2H), 4.02 (q, J=6.7 Hz, 1H), 4.14 (m, 2H), 4.93 (ddd, 1H, J=10.2, 2.2, 1.1 Hz, 1H), 4.99 (ddd, J=17.2, 2.2, 1.4 Hz, 1H), 5.20 (ddd, J=10.2, 1.7, 1.3 Hz, 1H), 5.29 (dq, J=17.2, 1.7 Hz, 1H), 5.81 (ddd, J=17.2, 10.2, 6.7 Hz, 1H), 5.93 (dddd, J=17.2, 10.2, 6.0, 5.2 Hz, 1H).

$^{13}$C-NMR (50 MHz, $CDCl_3$): δ(ppm)=18.7, 25.8, 28.5, 28.8, 29.0, 29.1, 29.3, 33.7, 64.9, 71.0, 74.0, 114.1, 117.7, 134.1, 139.1, 173.4.

(RS)-3-Methyl-1,4-dioxa-(E/Z)-6-cyclopentadecen-2-one (x=1, y=8, $R^1$=Me, $R^2$=H): 59.6 mg (0.21 mmol) of Ti(OiPr)$_4$ are added to a solution of 187 mg (0.7 mmol) of dec-9-enyl (RS)-2-allyloxy-propionate in 220 ml of $CH_2Cl_2$ and the mixture is refluxed for 1 h. 16.4 mg (0.02 mmol) of benzylidene-bis-(tricyclohexylphosphine)-dichlororuthenium, dissolved in 5 ml of $CH_2Cl_2$, are added and the mixture is refluxed for 20 h. After cooling to room temperature, the reaction solution is washed with 2×50 ml of 1N HCl, then dried over $Na_2SO_4$ before being filtered over a short silica gel column. The solvent is then removed on a rotary evaporator, giving 160 mg (95%) of a colorless oil.

Odor: musk, sweet-flowery, ambergris, erogenous, reminiscent of ambrette musk.

Isomerism details: excess:deficit isomer $^1$H-NMR (400 MHz, $CDCl_3$): δ(ppm)=1.23–1.46 (m, 10H), 1.40:1,41 (d, J=6.9:6.9 Hz, 3H), 1.57–1.74 (m, 2H), 1.91–2.14 (m, 2H), 3.86–4.12 (m, 2H), 4.01:4.03 (q, J=6.9:6.9 Hz, 1H), 4.20–4.44 (m, 2H), 5.46–5.67 (m, 2H).

$^{13}$C-NMR (50 MHz, $CDCl_3$): δ(ppm)=18.7:18.9, 23.3, 24.8, 26.0, 26.3, 26.8, 27.6, 31.0, 64.4:65.3, 71.3:65.7, 72.8:73.0, 127.1:126.2, 135.4:134.3, 173.7.

(RS)-3-Methyl-1,4-dioxacyclopentadecan-2-one (x=1, y=8, $R^1$=Me, $R^2$=H): 12 mg of Pd/C are added to a solution of 240 mg (1 mmol) of (RS)-3-methyl-1,4-dioxa-(E/Z)-6-cyclopentadecen-2-one and 10 ml of isopropanol. Hydrogenation is then carried out at room temperature and atmospheric pressure. After 3 h, the mixture is filtered over Celite with suction and the solvent is removed on a rotary evaporator. Flash chromatography (cyclohexane/EtOAc=30:1, $R_f$=0.28) over silica gel gives 177 mg (74%) of a colorless oil.

Odor: musk, sweet-flowery, ambergris, erogenous, animalic, reminiscent of ambrette musk and nitromusk.

$^1$H-NMR (200 MHz, $CDCl_3$): δ(ppm)=1.20–1.50 (m, 14H), 1.40 (d, J=6.8 Hz, 3H), 1.57–1.80 (m, 4H), 3.50 (m, 2H), 3.99 (q, J=6.8 Hz, 1H), 4.20 (ddd, J=6.1, 4.7, 1.3 Hz, 2H).

$^{13}$C-NMR (50 MHz, $CDCl_3$): δ(ppm)=18.6, 23.3, 24.5, 24.9, 25.2, 26.2, 26.3, 26.5, 27.7, 28.2, 64.9, 70.4, 75.6, 174.1.

Example 2.2

(S)-(-)-3-Methyl-1,4-dioxacyclopentadecan-2-one

Ethyl (S)-(-)-2-allyloxy-propionate (x=1, $R^1$=Me, $R^2$=H, $R^3$=Et): 7.08 g (60 mmol) of ethyl (S)-(-)-lactate are introduced into 120 ml of cyclohexane, and 25.0 g (120 mmol) of allyl trichloroacetimidate, dissolved in 30 ml of cyclohexane, are added thereto. 0.55 ml (6 mmol) of trifluoromethanesulfonic acid are then added and the mixture is stirred for 16 h. When the reaction is complete, the precipitated trichloroacetamide is filtered off with suction and washed with cyclohexane. The filtrate is washed with saturated $NaHCO_3$ solution, after which the organic phase is dried over $Na_2SO_4$, filtered and evaporated on a rotary evaporator. Flash-chromatographic purification (cyclohexane/EtOAc=10:1; $R_f$=0.27) gives 6.9 g (72%) of a colorless liquid.

Angle of rotation: $[α]_D^{20}$=−70.1°.

Enantiomeric purity: ee=95.2%.

Dec-9-enyl (S)-(-)-2-allyloxy-propionate (x=1, y=8, $R^1$=Me, $R^2$=H): 3.0 g (19 mmol) of ethyl 2-allyloxypropionate are introduced into 4.5 g (28.5 mmol) of 9-decen-1-ol, and 0.56 g (2 mmol) of Ti(OiPr)$_4$ are added. The mixture is then heated to 80° C. and stirred at a reduced pressure of 400 mbar for 5 h. A few drops of water are then added and the crude product is purified by means of flash chromatography (cyclohexane/EtOAc=25:1; $R_f$=0.21), giving 4.1 g (81%) of a colorless oil.

Angle of rotation: $[α]_D^{20}$=−46.60°.

Enantiomeric purity: ee=94.8%.

The ring closure olefin metathesis and subsequent hydrogenation were carried out analogously to the procedures described under 2.1. Only the angle of rotation and the enantiomeric purity are thus given here:

(S)-(-)-3-Methyl-1,4-dioxa-(E/Z)-6-cyclopentadecen-2-one (x=1, y=8, $R^1$=Me, $R^2$=H)

Odor: weakly musk, sweet-flowery, erogenous, weaker than the enantiomer mixture.

Angle of rotation: $[α]_D^{20}$=−20.0°.

Enantiomeric purity: the enantiomeric purity for the two E/Z isomers cannot be determined due to peak overlaps.

(S)-(-)-3-Methyl-1,4-dioxacyclopentadecan-2-one (x=1, y=8, $R^1$=Me, R=H)

Odor: musk, sweet-flowery, ambergris, erogenous, animalic, reminiscent of ambrette musk and nitromusk, weaker than the enantiomer mixture.

Angle of rotation: $[\alpha]_D^{20}=-23.0°$.

Enantiomeric purity: ee=95.2%.

The following antipodes are accessible in a corresponding way. For these, only the angle of rotation and the enantiomeric purity are therefore given:

Example 2.3

(R)-(+)-3-Methyl-1,4-dioxacyclopentadecan-2-one

Isobutyl R)-(+)-2-allyloxy-propionate (x=1, $R^1$=Me, $R^2$=H, $R^3$=i-Bu)

Angle of rotation: no angle of rotation determination since the compound was further used as crude product.

Enantiomeric purity: ee=99%.

Dec-9-enyl (R)-(+)-2-allyloxy-propionate (x=1, y=8, $R^1$=Me, $R^2$=H)

Angle of rotation: No angle of rotation determination since the compound was further used as crude product.

Enantiomeric purity: ee=99%.

(R)-(+)-3-Methyl-1,4-dioxa-(E/Z)-6-cyclopentadecen-2-one (x=1, y=8, $R^1$=Me, $R^2$=H)

Odor: musk, sweet-flowery, ambergris, erogenous, reminiscent of ambrette musk, more musk-like and erogenous than the (S)-(−)-enantiomer.

Angle of rotation: $[\alpha]_D^{20}=+20.0°$.

Enantiomeric purity: the enantiomeric purity for the two E/Z isomers cannot be determined due to peak overlapping.

(R)-(+)-3-Methyl-1,4-dioxacyclopentadecan-2-one (x=1, y=8, $R^1$=Me, $R^2$=H)

Odor: musk, sweet-flowery, ambergris, erogenous, animalic, reminiscent of ambrette musk and nitromusk, stronger than the (S)-(−)-enantiomer.

Angle of rotation: $[\alpha]_D^{20}=+20.4°$.

Enantiomeric purity: ee=99%.

The following compounds of Examples 3.1, 3.2, 3.3 have been prepared analogously to the procedures described under Example 2.1. For these, only the spectroscopic data are therefore given:

Example 3.1

(RS)-3-Methyl-1,4-dioxacyclohexadecan-2-one

Undec-10-enyl (RS)-2-allyloxy-propionate (x=1, y=9, $R^1$=Me, $R^2$=H)

$^1$H-NMR (200 MHz, CDCl$_3$): δ(ppm)=1.25–1.44 (m, 12), 1.42 (d, J=6.9 Hz, 3H), 1.57–1.76 (m, 2), 1.98–2.11 (m, 2H), 3.94 (ddd, J=12.5, 6.1, 1.3 Hz, 2H), 4.01 (q, J=6.9 Hz, 1H), 4.13 (m, 2H), 4.93 (ddd, J=10.2, 2.2, 1.2 Hz, 1H), 4.99 (ddd, J=17.1, 2.2, 1.5 Hz, 1H), 5.20 (ddd, J=10.3, 1.7, 1.1 Hz, 1H), 5.29 (dq, J=17.3, 1.7 Hz, 1H), 5.81 (ddd, J=17.1, 10.2, 6.7 Hz, 1H), 5.95 (ddd, J=17.3, 10.3, 6.2 Hz, 1H).

$^{13}$C-NMR (50 MHz, CDCl$_3$): δ(ppm)=18.7, 25.8, 28.5, 28.9, 29.0, 29.1, 29.3, 29.4, 33.8, 64.9, 71.0, 74.0, 114.1, 117.6, 134.1, 139.1, 173.4.

(RS)-3-Methyl-1,4-dioxa-(E/Z)-6-cyclohexadecen-2-one (x=1, y=9, $R^1$=Me, $R^2$=H)

Odor: musk, sweet-woody, ambergris, erogenous, animalic, reminiscent of ambrette musk.

Isomerism details: excess:deficit isomer $^1$H-NMR (200 MHz, CDCl$_3$): δ(ppm)=1.22–1.53 (m, 12 H), 1.40:1.42 (d, J=6.8:6.8 Hz, 3H), 1.65 (m, 2H), 2.11:2.05 (m, 2H), 3.96–4.36 (m, 4H), 4.10:4.02 (q, J=6.8:6.8 Hz, 1H), 5.48–5.69 (m, 2H).

$^{13}$C-NMR (50 MHz, CDCl$_3$): δ(ppm)=18.2:18.8, 24.9, 25.4, 26.1, 26.3, 27.1, 27.5, 28.0, 31.3, 64.6:64.7, 69.8:66.2, 71.5:74.1, 126.4:125.9, 135.7:133.6, 173.4.

(RS)-3-Methyl-1,4-dioxacyclohexadecan-2-one (x=1, y=9, $R^1$=Me, $R^2$=H)

Odor: musk, sweet-woody, ambergris, erogenous, animalic, reminiscent of ambrette musk and nitromusk.

$^1$H-NMR (200 MHz, CDCl$_3$): δ(ppm)=1.25–1.50 (m, 16H), 1.40 (d, J=6.7 Hz, 3H), 1.53–1.76 (m, 4H), 3.31–3.63 (m, 2H), 3.99 (q, J=6.7 Hz, 1H), 4.21 (dd, J=5.6, 5.0 Hz, 2H).

$^{13}$C-NMR (50 MHz, CDCl$_3$): δ(ppm)=18.1, 24.2, 24.6, 25.4, 26.5, 26.6, 26.7, 26.8, 26.9, 28.4, 28.7, 64.8, 69.9, 75.5, 173.6.

Example 3.2

(S)-(−)-3-Methyl-1,4-dioxacyclohexadecan-2-one

Undec-10-enyl (S)-(−)-2-allyloxy-propionate (x=1, y=9, $R^1$=Me, $R^2$=H):

Angle of rotation: $[\alpha]_D^{20}=-36.0°$.

Enantiomeric purity: ee=94.6%.

(S)-(−)-3-Methyl-1,4-dioxa-(E/Z)-6-cyclohexadecen-2-one (x=1, y=9, $R^1$=Me, $R^2$=H)

Odor: weakly musk, sweet-woody, erogenous.

Angle of rotation: $[\alpha]_D^{20}=-23.0°$.

Enantiomeric purity: the enantiomeric purity for the two E/Z isomers cannot be determined due to peak overlapping.

(S)-(−)-3-Methyl-1,4-dioxacycloexadecan-2-one (x=1, y=9, $R^1$=Me, $R^2$=H)

Odor: musk, sweet-woody, ambergris, erogenous, animalic, reminiscent of ambrette musk and nitromusk, weaker than the enantiomer mixture.

Angle of rotation: $[\alpha]_D^{20}=-16.0°$.

Enantiomeric purity: ee=95.2%.

Example 3.3

(R)-(+)-3-Methyl-1,4-dioxacyclohexadecan-2-one

Undec-10-enyl (R)-(+)-2-allyloxy-propionate (x=1, y=9, $R^1$=Me, $R^2$=H)

Angle of rotation: no angle of rotation determination since the compound was used further as crude product.

Enantiomeric purity: ee=99%.

(R)-(+)-3-Methyl-1,4-dioxa-(E/Z)-6-cyclohexadecen-2-one (x=1, y=9, $R^1$=Me, $R^2$=H)

Odor: musk, sweet-woody, ambergris, erogenous, animalic, reminiscent of ambrette musk, stronger than the enantiomer mixture.

Angle of rotation: $[\alpha]_D^{20}=+28.2°$.

Enantiomeric purity: the enantiomeric purity for the two E/Z isomers cannot be determined due to peak overlapping.

(R)-(+)-3-Methyl-1,4-dioxacyclohexadecan-2-one (x=1, y=9, $R^1$=Me, $R^2$=H)

Odor: musk, sweet-woody, ambergris, erogenous, animalic, reminiscent of ambrette musk and nitromusk, stronger than the (S)-(−)-enantiomer.

Angle of rotation: $[\alpha]_D^{20}=+15.4°$.

Enantiomeric purity: ee=99%.

Example 4

1,4-Dioxacyclopentadecan-2-one

2-Allyloxy-acetic acid (x=1, Y=OH, $R^1$, $R^2$=H): 1.8 g (30 mmol) of allyl alcohol, dissolved in 10 ml of THF, are added to a suspension of 2.4 g (60 mmol) of NaH in 30 ml of THF. 3.4 g (25 mmol) of bromoacetic acid, dissolved in 20 ml of THF, are then added dropwise. The mixture is then refluxed for 6 h. After this time, the mixture is cooled and the reaction is quenched with 40 ml of 2N HCl. The aqueous phase is extracted three times with EtOAc. The combined organic phases are dried over Na$_2$SO$_4$, filtered and evaporated to dryness on a rotary evaporator, giving 3.8 g of crude product (GC purity 90.3%), which is used in the next reactions without further purification.

Dec-9-enyl 2-allyloxy-acetate (x=1, y=9, R$^1$, R$^2$ =H): 2.5 g of crude 2-allyloxyacetic acid are introduced into 40 ml of toluene, and 4.7 g (30 mmol) of 9-decen-1-ol and 0.38 g (2.0 mmol) of p-toluenesulfonic acid are added. The mixture is then heated with a water separator until visible amounts of water no longer separate out. The mixture is then cooled, and the organic phase is washed once with saturated NaHCO$_3$ solution, dried over Na$_2$SO$_4$ and filtered, and the product is freed from the solvent. Flash chromatography (cyclohexane/EtOAc=20:1, R$_f$=0.29) gives 3.1 g (62%) of dec-9-enyl 2-allyloxy-acetate as a colorless oil.

$^1$H-NMR (200 MHz, CDCl$_3$): δ(ppm)=1.20–1.45 (m, 10H), 1.55–1.73 (m, 2H), 1.96–2.02 (m, 2H), 4.08 (s, 2H), 4.10 (dt, J=5.8, 1.2 Hz, 2H), 4.16 (t, J=6.7 Hz, 2H), 4.93 (ddd, J=10.3, 2.2, 1.2 Hz, 1H), 4.99 (ddd, J=17.3, 2.2, 1.5 Hz, 1H), 5.24 (ddd, J=10.3, 1.7, 1.2 Hz, 1H), 5.31 (dq, J=17.3, 1.7 Hz, 1H), 5.81 (ddd, J=17.3, 10.3, 6.6 Hz, 1H), 5.93 (ddd, J=17.3, 10.3, 5.8 Hz, 1H).

$^{13}$C-NMR (50 MHz, CDCl$_3$): δ(ppm)=25.8, 28.5, 28.8, 29.0, 29.1, 29.3, 33.7, 64.9, 67.1, 72.3, 114.1, 118.2, 133.7, 139.1, 170.4.

The ring closure olefin metathesis and also the subsequent hydrogenation are carried out analogously to the synthesis procedures described under Example 2.1, meaning that only the spectroscopic data are given here:

1,4-Dioxa-(E/Z)-6-cyclopentadecen-2-one (x=1, y=8, R$^1$, R$^2$=H)

Odor: musk, metallic, reminiscent of a hot iron.
Isomerism details: excess:deficit isomer
$^1$H-NMR (200 MHz, CDCl$_3$): δ(ppm)=1.20–1.50 (m, 10H), 1.55–1.80 (m, 2H), 2.0–2.16 (m, 2H), 4.09 (s, 2H), 4.11–4.33 (m, 4H), 5.43–5.75 (m, 2H).
$^{13}$C-NMR (50 MHz, CDCl$_3$): δ(ppm)=23.1, 25.2, 26.1, 26.5, 27.3, 27.5, 31.2, 64.2:65.3, 65.7:66.1, 72.6, 126.6:125.5, 136.6:135.6, 171.2.

4-Dioxacyclopentadecan-2-one (x=1, y=8, R$^1$, R$^2$=H)

Odor: musk, sweet-flowery, erogenous, reminiscent of musk ambrette.
$^1$H-NMR (200 MHz, CDCl$_3$): δ(ppm)=1.30–1.51 (m, 14H), 1.60–1.80 (m, 4H), 3.52 (t, J=6.6 Hz, 2H), 4.11 (s, 2H), 4.22 (dd, J=5.1, 4.4 Hz, 2H).
$^{13}$C-NMR (50 MHz, CDCl$_3$): δ(ppm)=23.7, 24.7, 25.3, 25.5, 26.2, 26.6, 26.9, 27.7, 28.0, 65.3, 69.3, 71.9, 171.3.

The following compounds are accessible in a corresponding way. For these, only the spectroscopic data are therefore given:

Example 5

1,4-Dioxacyclohexadecan-2-one

Undec-10-enyl 2-allyloxy-acetate (x=1, y=9, R$^1$, R$^2$=H)
$^1$H-NMR (200 MHz, CDCl$_3$): δ(ppm)=1.20–1.45 (m, 12H), 1.55–1.73 (m, 2H), 1.96–2.11 (m, 2H), 4.08 (s, 2H), 4.10 (dt, J=5.8, 1.4 Hz, 2H), 4.16 (t, J=6.7 Hz, 2H), 4.93 (ddd, J=10.2, 2.2, 1.3 Hz, 1H), 4.99 (ddd, J=17.1, 2.2, 1.4 Hz, 1H), 5.24 (ddd, J=10.2, 1.5, 1.2 Hz, 1H), 5.31 (dq, J=17.2, 1.5 Hz, 1H), 5.81 (ddd, J=17.2, 10.2, 6.7 Hz, 1H), 5.93 (ddd, J=17.2, 10.2, 5.8 Hz, 1H).
$^{13}$C-NMR (50 MHz, CDCl$_3$): δ(ppm)=25.8, 28.5, 28.9, 29.0, 29.2, 29.3, 29.4, 33.8, 65.0, 67.1, 72.3, 114.1, 118.1, 133.7, 139.1, 170.4.

1,4-Dioxa-(E/Z)-6-cyclohexadecen-2-one (x=1, y=9, R$^1$, R$^2$=H)

Odor: musk, woody, technically reminiscent of a hot iron.
Isomerism details: excess:deficit isomer
$^1$H-NMR (200 MHz, CDCl$_3$): δ(ppm)=1.20–1.50 (m, 12H), 1.61–1.78 (m, 2H), 2.00–2.20 (m, 2H), 4.07–4.14 (m, 2H), 4.10:4.11 (s, 2H), 4.18–4.29 (m, 2H), 5.41–5.76 (m, 2H).
$^{13}$C-NMR (50 MHz, CDCl$_3$): δ(ppm)=25.3, 25.9, 26.4, 26.9, 27.6, 27.7, 27.9, 31.6, 64.7:66.7, 64.8:66.8, 70.8, 125.8:125.2, 137.3:135.1, 170.5.

1,4-Dioxacyclohexadecan-2-one (x=1, y=9, R$^1$, R$^2$=H)

Odor: musk, ambergris, erogenous, animalic, reminiscent of musk tincture, musk ambrette and nitromusk.
$^1$H-NMR (200 MHz, CDCl$_3$): δ(ppm)=1.25–1.51 (m, 16H), 1.55–1.75 (m, 2H), 3.53 (t, J=5.8 Hz, 2H), 4.08 (s, 2H), 4.24 (dd, J=5.2, 5.1 Hz, 2H).
$^{13}$C-NMR (50 MHz, CDCl$_3$): δ(ppm)=24.2, 24.3, 25.3, 25.4, 26.5, 26.6, 26.8, 26.9, 28.1, 28.5, 64.8, 69.0, 71.2, 170.5.

Example 6

1,4-Dioxa-(E/Z)-7-cyclohexadecen-2-one

Dec-9-enyl 2-(3-butenyloxy)-acetate (x=2, y=8, R$^1$, R$^2$=H)
$^1$H-NMR (200 MHz, CDCl$_3$): δ(ppm)=1.20–1.41 (m, 10H), 1.57–1.71 (m, 2H), 1.98–2.12 (m, 2H), 2.40 (qd, J=6.7, 1.4 Hz, 2H), 3.60 (t, J=6.6 Hz, 2H), 4.09 (s, 2H), 4.15 (t, J=6.8 Hz, 2H), 4.92 (ddd, J=10.3, 2.2, 1.3 Hz, 1H), 4.95 (ddd, J=16.4, 2.2, 1.4 Hz, 1H), 5.11 (ddd, J=10.3, 1.5, 1.2 Hz, 1H), 5.18 (dq, J=16.4, 1.4 Hz, 1H), 5.75 (ddd, J=16.4, 10.3, 6.6 Hz, 1H), 5.93 (ddd, J=16.4, 10.3, 5.8 Hz, 1H).
$^{13}$C-NMR (50 MHz, CDCl$_3$): δ(ppm)=25.8, 28.6, 28.9, 29.0, 29.2, 29.3, 33.8, 34.0, 65.0, 68.3, 71.0, 114.2, 116.7, 134.8, 139.1, 170.6.

1,4-Dioxa-(E/Z)-7-cyclohexadecen-2-one (x=2, y=8, R$^1$, R$^2$=H)

Odor: musk, erogenous, sweet-woody, metallic, reminiscent of a hot iron.
Isomerism details: excess:deficit isomer
$^1$H-NMR (200 MHz, CDCl$_3$): δ(ppm)=1.20–1.50 (m, 10H), 1.59–1.73 (m, 2H), 1.98–2.12 (m, 2H), 2.25–2.48 (m, 2H), 3.44–3.62 (m, 2H), 4.09:4.11 ( s, 2H), 4.18–4.30 (m, 2H), 5.40–5.50 (m, 2H).
$^{13}$C-NMR (50 MHz, CDCl$_3$): δ(ppm)=23.8, 25.3, 26.7, 26.8, 27.5, 27.6, 31.6, 33.1, 65.0:64.2, 69.3:69.2, 71.3:71.4, 127.5:125.0, 132.2, 170.4.

Example 7

1,4-Dioxa (E/Z)-7-cycloheptadecen-2-one

Undec-10-enyl 2-(3-butenyloxy)-acetate (x=2, y=9, R$^1$, R$^2$=H)
$^1$H-NMR (200 MHz, CDCl$_3$): δ(ppm)=1.20–1.48 (m, 12H), 1.55–1.74 (m, 2H), 1.97–2.12 (m, 2H), 2.40 (qd, J=6.9, 1.2 Hz, 2H), 3.60 (t, J=6.7 Hz, 2H), 4.0 (s, 2H), 4.15 (t, J=6.8 Hz, 2H), 4.92 (ddd, J=10.2, 2.2, 1.4 Hz, 1H), 4.96 (ddd, J=16.3, 2.2, 1.4 Hz, 1H), 5.08 (ddd, J=10.3, 1.4, 1.2 Hz, 1H), 5.17 (dq, J=16.5, 1.4 Hz, 1H), 5.75 (ddd, J=16.3, 10.3, 6.5 Hz, 1H), 5.93 (ddd, J=16.5, 10.3, 5.7 Hz, 1H).
$^{13}$C-NMR (50 MHz, CDCl$_3$): δ(ppm)=25.8, 28.5, 28.8, 29.0, 29.1, 29.3, 29.4, 33.8, 34.0, 64.9, 68.3, 71.0, 114.1, 116.6, 134.7, 139.1, 170.5.

1,4-Dioxa-(E/Z)-7-cycloheptadecen-2-one (x=2, y=9, R$^1$, R$^2$=H)

Odor: musk, erogenous, sweet-woody.
Isomerism details: excess:deficit isomer
$^1$H-NMR (200 MHz, CDCl$_3$): δ(ppm)=1.21–1.51 (m, 12H), 1.60–1.78 (m, 2H), 2.00–2.18 (m, 2H), 2.26–2.50 (m, 2H), 3.48–3.64 (m, 2H), 4.12 (s, 2H), 4.19–4.29 (m, 2H), 5.34–5.51 (m, 2H).

$^{13}$C-NMR (50 MHz, CDCl$_3$): δ(ppm)=26.9, 27.6, 28.0, 28.1, 28.2, 28.4, 28.5, 31.5, 32.9, 65.4:65.2, 69.2:68.9, 71.6, 126.7:124.4, 132.6, 170.7

Example 8

(RS)-3-Methyl-1,4-dioxa-(E/Z)-7-cyclohexadecen -2-one

Dec-9-enyl 2-(3-butenyloxy)-propionate (x=2, y=8, R$^1$=Me, R$^2$=H)

$^1$H-NMR (200 MHz, CDCl$_3$): δ(ppm)=1.26–1.44 (m, 10H), 1.40 (d, J=6.9 Hz, 3H), 1.60–1.70 (m, 2H), 1.98–2.07 (m, 2H), 2.37 (qt, J=6.9, 1.5 Hz, 2H), 3.42 (dt, J=8.5, 6.8 Hz, 1H), 3.64 (dt, J=8.5, 6.8 Hz, 1H), 3.81 (q, J=6.8 Hz, 1H), 4.14 (td, J=6.8, 2.6 Hz, 2H), 4.90 (ddd, J=10.2, 2.2, 1.4 Hz, 1H), 4.95 (ddd, J=16.3, 2.2, 1.4 Hz, 1H), 5.07 (ddd, J=10.3, 1.4, 1.2 Hz, 1H), 5.15 (dq, J=16.5, 1.4 Hz, 1H), 5.74 (ddd, J=16.3, 10.3, 6.5 Hz, 1H), 5.91 (ddd, J=16.5, 10.3, 5.7 Hz, 1H).

$^{13}$C-NMR (50 MHz, CDCl$_3$): δ(ppm)=18.7, 25.8, 28.5, 28.8, 28.9, 29.1, 29.3, 33.7, 34.1, 64.8, 69.4, 74.9, 114.0, 116.4, 134.7, 139.0, 173.3.

(RS)-3-Methyl-1,4-dioxa-(E/Z)-7-cyclohexadecen-2-one (x=2, y=8, R$^1$=Me, R$^2$=H)

Odor: musk, woody, metallic, reminiscent of a hot iron.

Isomerism details: excess:deficit isomer $^1$H-NMR (200 MHz, CDCl$_3$): δ(ppm)=1.22–1.42 (m, 10H), 1.40:1.42 (d, J=6.8 Hz, 3H), 1.55–1.72 (m, 2H), 1.96–2.09 (m, 2H), 2.19–2.38 (m,2H), 3.37–3.57 (m, 2H), 3.98:4.00 (q, J=6.8 Hz, 1H), 4.10–4.30 (m, 2H), 5.39–5.49 (m, 2H).

$^{13}$C-NMR (50 MHz, CDCl$_3$): δ(ppm)=18.2, 24.5, 24.9, 26.8, 27.1, 28.0, 28.1, 31.1, 33.1, 65.0:64.1, 70.4.70.1, 76.8, 127.5:124.5, 132.1, 173.4.

Example 9

(RS)-3-Methyl-1,4-dioxacycloheptadecan-2-one

Undec-10-enyl 2-(3-butenyloxy)-propionate (x=2, y=9, R$^1$=Me, R$^2$=H)

$^1$H-NMR (200 MHz, CDCl$_3$): δ(ppm)=1.24–1.42 (m, 12H), 1.40 (d, J=6.8 Hz, 3H), 1.58–1.70 (m, 2H), 1.97–2.10 (m, 2H), 2.37 (qt, J=6.9, 1.4 Hz, 2H), 3.42 (dt, J=9.0, 6.9 Hz, 1H), 3.64 (dt, J=9.0, 6.9 Hz, 1H), 3.96 (q, J=6.8 Hz, 1H), 4.15 (td, J=6.5, 2.6 Hz, 2H), 4.91 (ddd, J=10.1, 2.2, 1.4 Hz, 1H), 4.95 (ddd, J=17.0, 2.2, 1.4 Hz, 1H), 5.07 (ddd, J=10.2, 1.4, 1.2 Hz, 1H), 5.15 (dq, J=17.2, 1.4 Hz, 1H), 5.74 (ddd, J=17.0, 10.1, 6.5 Hz, 1H), 5.91 (ddd, J=17.2, 10.2, 5.7 Hz, 1H).

$^{13}$C-NMR (50 MHz, CDCl$_3$): δ(ppm)=18.6, 25.8, 28.5, 28.8, 29.0, 29.1, 29.3, 29.4, 33.7, 34.1, 64.8, 69.4, 74.9, 114.0, 116.4, 134.7, 139.0, 173.3.

(RS)-3-Methyl-1,4-dioxa-(E/Z)-7-cycloheptadecen-2-one (x=2, y=9, R$^1$=Me, R$^2$=H)

Odor: musk, erogenous, sweet-woody.

$^1$H-NMR (200 MHz, CDCl$_3$): δ(ppm)=1.20–1.44 (m, 12H), 1.40:1.42 (d, J=6.8 Hz, 3H), 1.60–1.75 (m, 2H), 1.98–2.10 (m, 2H), 2.25–2.37 (m,2H), 3.34–3.60 (m, 2H), 4.00:3.98 (q, J=6.8 Hz, 1H), 4.15–4.28 (m, 2H), 5.40–5.50 (m, 2H).

$^{13}$C-NMR (50 MHz, CDCl$_3$): δ(ppm)=18.5:18.8, 25.8, 27.1, 27.5, 27.7, 27.8, 28.6, 28.7, 31.6, 32.9, 65.0, 70.5:70.2, 75.5:75.7, 126.0:124.0, 132.9:132.5, 173.6

(RS)-3-Methyl-1,4-dioxacycloheptadecan-2-one (x=2, y=9, R$^1$=Me, R$^2$=H)

Odor: musk, sweet-woody, ambergris, erogenous, animalic, reminiscent of ambrette musk.

$^1$H-NMR (200 MHz, CDCl$_3$): δ(ppm)=1.26–1.44 (m, 18H), 1.40 (d, J=6.8 Hz, 3H), 1.55–1.75 (m, 4H), 3.38–3.60 (m, 2H), 3.79 (q, J=6.8 Hz, 1H), 4.10–4.30 (m, 2H).

$^{13}$C-NMR (50 MHz, CDCl$_3$): δ(ppm)=18.6, 24.7, 25.3, 26.1, 26.4, 26.6, 26.7, 27.1, 27.3, 27.4, 28.6, 28.7, 64.9, 70.3, 75.5, 173.7.

Example 10

The present perfume oil is used for the perfuming of many different types of cosmetic products.

Composition

| Ingredients | Parts by weight |
|---|---|
| 1. Citrophoral Base (H&R) | 5.0 |
| 2. Aldehyde C10 10% in BA | 5.0 |
| 3. Aldehyde C11 MOA 10% in BA | 3.0 |
| 4. Farenal (H&R) | 3.0 |
| 5. Aldehyde C11 10% in IPM | 5.0 |
| 6. Citroxal 50% in DEP | 2.0 |
| 7. trans Hex-2-enol 10% in BA | 2.0 |
| 8. Vertocitral (H&R) | 1.0 |
| 9. Linalyl acetate | 45.0 |
| 10. Citrylal (H&R) | 5.0 |
| 11. Mandarinal (Firmenich) | 4.0 |
| 12. Lilial (Givaudan Roure) | 75.0 |
| 13. Lyral (IFF) | 75.0 |
| 14. Profarnesol (H&R) | 5.0 |
| 15. Nerolidol | 5.0 |
| 16. Linalool | 45.0 |
| 17. Geranium oil, African | 5.0 |
| 18. Phenylethyl alcohol | 75.0 |
| 19. Geraniol | 15.0 |
| 20. Nerol | 10.0 |
| 21. Hexylcinnamaldehyde alpha | 50.0 |
| 22. Methyl dihydrojasmonate | 15.0 |
| 23. Benzyl salicylate | 100.0 |
| 24. trans,cis-2-Nonadienol 0.1% in IPM | 5.0 |
| 25. Allyl ionone (Givaudan Roure) | 3.0 |
| 26. Isomethyl ionone, gamma | 75.0 |
| 27. Eugenol | 7.0 |
| 28. Cedryl acetate | 40.0 |
| 29. Sandolen (H&R) | 5.0 |
| 30. Citral | 5.0 |

BA = benzyl alcohol; IPM = isopropyl myristate; DEP = diethyl phtalate

The addition of a) 355 parts by weight of 3-methyl-1,4-dioxacyclopentadecan-2-one (total 1000 parts by weight) leads to a significantly perceptible harmonization of the fresh top note with the rosy-flowery middle note. Moreover, with 3-methyl-1,4-dioxacyclopentadecan-2-one, effects reminiscent of nitromusk are achieved and the fine erogenous musk note imparts excellent radiance and increased adhesion to the present composition. In this connection, the grand character of 3-methyl-1,4-dioxacyclopentadecan-2-one in particular predominates compared with compositions containing conventional musk fragrances.

b) 55 parts by weight of 3-methyl-1,4-dioxacyclopentadecan-2-one (sum 700 parts by weight) impart to the composition an animalic musk note which is not achieved with existing musk fragrances. In addition, the overall composition acquires body and appears grander.

What is claimed is:

1. A macrocyclic compound of the formula

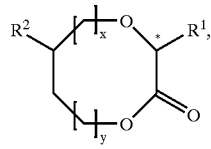

(I)

wherein the dashed bond is a single or a E/Z double bond and when the dashed bond is a double bond, the compounds are in the E or Z form, wherein compounds having a chiral center are in (R) or (S) form, or are present as an enantiomer mixture, wherein $R^1$ and $R^2$ are the same or different and are a hydrogen or a lower alkyl, wherein x is a saturated alkylene chain having 1 to 4 carbon atoms, wherein y is a saturated alkylene chain having 4 to 10 carbon atoms, and wherein saturated compounds in which $R^1$ and $R^2$ are hydrogen and x+y=11 carbon atoms and in which $R^1$ is methyl and $R^2$ is hydrogen and x+y=8 carbon atoms are excluded.

2. A macrocyclic compound according to claim 1, wherein $R^1$ and $R^2$ are the same or different and are selected from the group consisting of hydrogen, methyl or ethyl, wherein x a is an alkylene chain having 1, 2 and 4 carbon atoms, wherein y is an alkylene chain having 4, 8 and 9 carbon atoms, and wherein saturated compounds in which $R^1$ and $R^2$ are hydrogen and x+y=11 carbon atoms and in which $R^1$ is methyl and $R^2$ is hydrogen and x+y=8 carbon atoms are excluded.

3. A macrocyclic compound according to claim 1, wherein the compound is selected from the group consisting of 1,4-dioxa(E/Z)-9-cyclotetradecen-2-one, 1,4-dioxacyclotetradecan-2-one, 3-methyl-1,4-dioxa-(E/Z)-6-cyclopentadecen-2-one, 3-methyl-1,4-dioxacyclopentadecan-2-one, 1,4-dioxa-(E/Z)-6-cyclopentadecen-2-one, 1,4-dioxacyclopentadecan-2-one, 3-methyl-1,4-dioxa-(E/Z)-6-cyclohexadecen-2-one, 3-methyl-1,4-dioxacyclohexadecan-2-one, 1,4-dioxa-(E/Z)-6-cyclohexadecen-2-one, 1,4-dioxacyclohexadecan-2-one, 1,4-dioxa-(E/Z)-7-cyclohexadecen-2-one, 1,4-dioxa (E/Z)-7-cycloheptadecen-2-one, 3-methyl-1,4-dioxa-(E/Z)-7-cyclohexadecen-2-one, 3-methyl-1,4-dioxa-(E/Z)-7-cycloheptadecen-2-one, and 3-methyl-1,4-dioxacycloheptadecan-2-one.

4. A doubly terminally unsaturated 2-alkenyloxycarboxylic alkenyl ester of the formula

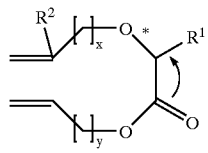

wherein compounds having a chiral center are in (R) or (S) form, or are present as an enantiomer mixture, and wherein $R^1$ and $R^2$ are the same or different and are a hydrogen or a lower alkyl, wherein x is a saturated alkylene chain having 1 to 4 carbon atoms, and wherein y is a saturated alkylene chain having 4 to 10 carbon atoms.

5. A doubly terminally unsaturated 2-alkenyloxycarboxylic alkenyl ester according to claim 4, wherein $R^1$ and $R^2$ are the same or different and are selected from the group consisting of hydrogen, methyl and ethyl, wherein x is an alkylene chain having 1, 2 and 4 carbon atoms, and wherein y is an alkylene chain having 4, 8 and 9 carbon atoms.

6. A process for the preparation of macrocyclic compounds of the formula

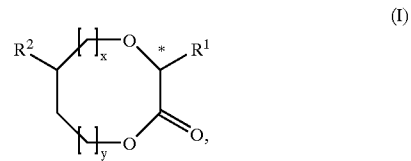

(I)

wherein the dashed bond is a single or a E/Z double bond and when the dashed bond is a double bond, the compounds are in the E or Z form, wherein compounds having a chiral center are present as an enantiomer mixture, wherein $R^1$ and $R^2$ are the same or different and are a hydrogen or a lower alkyl, wherein x is a saturated alkylene chain having 1 to 4 carbon atoms, and wherein y is a saturated alkylene chain having 4 to 10 carbon atoms, comprising the steps of etherfying a starting material to form a 2-alkenyloxycarboxylic acid or a 2-alkenyloxycarboxylic ester, wherein the starting material is an alkylcarboxylic acid or ester derived in the 2 position and of the formula

(II)

wherein
$R^1$ has the meaning given above, and
$R^3$ is selected from the group consisting of OH, Cl, and Br, and
$R^4$ is selected from the group consisting of OH, OMe and OEt,
esterfying the 2-alkenyloxycarboxylic acid or a 2-alkenyloxycarboxylic alkenyl ester to form an unsaturated 2-alkenyloxycarboxylic alkenyl ester, and then closing the open ring of the unsaturated 2-alkenyloxycarboxylic alkenyl ester by olefin metathesis to form a unsaturated 1,4 dioxacycloalken 2 ones.

7. A process for the preparation of chiral macrocyclic compounds of the formula

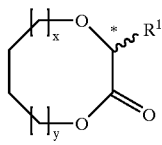

(I)

wherein the dashed bond is a single or E/Z double bond and when the dashed bond is a double bond, the compounds are in the E and Z form,
wherein compounds having a chiral center are present in(R) or (S) form,
wherein $R^1$ is a lower alkyl,
wherein x is a saturated alkylene chain having 1 to 4 carbon atoms, and
wherein y is a saturated alkylene chain having 4 to 10 carbon atoms, comprising the steps of etherfying a starting material under acidic, nonracemizing conditions to form a chiral (R)- or (S)-2-alkenyloxycarboxylic alkyl ester
wherein the starting material is a (S)-2- or (R)-2-hydroxycarboxylic alkyl ester of the formula

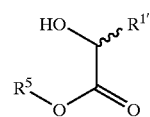

(II)

wherein
$R^{1'}$ has the meaning given above, and
$R^5$ is a $C_1$ to $C_8$ alkyl radical,
transesterfying the chiral (R)- or (S)-2-alkenyloxycarboxylic alkyl ester in the presence of a Lewis Acid to form an unsaturated 2-alkenyloxycarboxylic alkenyl ester,
and then closing the open ring of the unsaturated 2-alkenyloxycarboxylic alkenyl ester by olefin metathesis to form a unsaturated 3-alkyl-1,4-dioxacycloalken-2-ones.

8. A fragrance comprising macrocyclic compounds of the formula

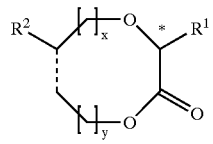

wherein the dashed bond is a single or a E/Z double bond and when a double bond is present, the compounds can be in the E or Z form,
wherein compounds having a chiral center are in (R) or (S) form, or are present as an enantiomer mixture, wherein $R^1$ and $R^2$ are the same or different and are a hydrogen or a lower alkyl,
wherein x is a saturated alkylene chain having 1 to 4 carbon atoms,
wherein y is a saturated alkylene chain having 4 to 10 carbon atoms,
and wherein saturated compounds
in which $R^1$ and $R^2$ are hydrogen and x+y=11 carbon atoms and
in which $R^1$ is methyl and $R^2$ is hydrogen and x+y=8 carbon atoms, are excluded.

9. A fragrance composition comprising macrocyclic compounds of the formula

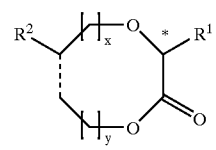

wherein the dashed bond is a single or a E/Z double bond and when the dashed bond is a double bond, the compounds can be in the E or Z form,
wherein compounds having a chiral center are in (R) or (S) form, or are present as an enantiomer mixture,
wherein $R^1$ and $R^2$ are identical or different and are hydrogen or lower alkyl,
wherein x is a saturated alkylene chain having 1 to 4 carbon atoms,
wherein y is a saturated alkylene chain having 4 to 10 carbon atoms, and wherein saturated compounds
in which $R^1$ and $R^2$ are hydrogen and x+y=11 carbon atoms and
in which $R^1$ is methyl and $R^2$ is hydrogen and x+y=8 carbon atoms, are excluded.

10. The fragrance composition according to claim 9, comprising 1 to 40% by weight of a macrocyclic 1,4-dioxacycloalkan-2-ones and a macrocyclic 1,4-dioxacycloalken-2-ones.

11. The fragrance composition according to claim 9, wherein the fragrance composition has a musk odor.

12. The process according to claim 6, further comprising the step of hydrogenating the unsaturated 1,4-dioxacycloalken-2-ones.

13. The process according to claim 7, further comprising the step of hydrogenating the unsaturated 3-alkyl-1,4-dioxacycloalken-2-ones.

14. A macrocyclic compound according to claim 1, wherein the compound is a 1,4-dioxacycloalkan-2-one or 1,4-dioxacycloalken-2-one.

15. A process according to claim 6 wherein the macrocyclic compound is a 1,4-dioxacycloalken-2-ones.

16. A process according to claim 12, wherein the macrocyclic compound is a 1,4-dioxacycloalkan-2-ones.

17. A process according to claim 7, wherein the macrocyclic compound is a 3-alkyl-1,4-dioxacycloalken-2-ones.

18. A process according to claim 13, wherein the macrocyclic compound is a 3-alkyl-1,4-dioxacycloalkan-2-ones.

* * * * *

UNITED STATES PATENT AND TRADEMARK OFFICE
CERTIFICATE OF CORRECTION

PATENT NO. : 6,573,391 B1
DATED : June 3, 2003
INVENTOR(S) : Eh et al.

It is certified that error appears in the above-identified patent and that said Letters Patent is hereby corrected as shown below:

Columns 7 and 8,
The formula should read:

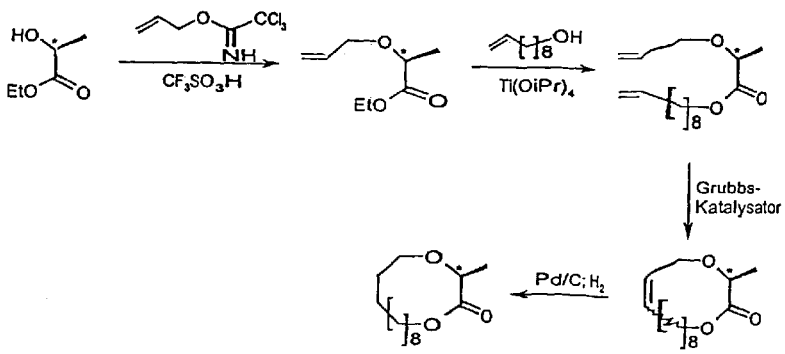

Signed and Sealed this

Twenty-fourth Day of August, 2004

JON W. DUDAS
*Director of the United States Patent and Trademark Office*